(12) United States Patent
Hovanes et al.

(10) Patent No.: US 6,605,103 B2
(45) Date of Patent: Aug. 12, 2003

(54) SYSTEM AND METHOD FOR CONTROLLING PRESSURE IN A SURGICAL TOURNIQUET

(75) Inventors: Michael E. Hovanes, Redmond, WA (US); Don S. Schmitt, Wauwatosa, WA (US)

(73) Assignee: Instrumed, Inc., Woodinville, WA (US)

( * ) Notice: Subject to any disclaimer, the term of this patent is extended or adjusted under 35 U.S.C. 154(b) by 61 days.

(21) Appl. No.: 09/955,763

(22) Filed: Sep. 19, 2001

(65) Prior Publication Data

US 2002/0016610 A1 Feb. 7, 2002

Related U.S. Application Data

(63) Continuation-in-part of application No. 09/504,131, filed on Feb. 15, 2000, now Pat. No. 6,475,228, which is a continuation of application No. 09/280,312, filed on Mar. 29, 1999, now Pat. No. 6,051,016.

(51) Int. Cl.[7] .............................................. A61B 17/12
(52) U.S. Cl. ...................................... 606/202; 606/203
(58) Field of Search ................................ 606/202, 201, 606/203; 128/681, 327, 680, 686

(56) References Cited

U.S. PATENT DOCUMENTS

| 4,469,099 A | 9/1984 | McEwen | |
|---|---|---|---|
| 4,469,099 A | 9/1984 | McEwen | |
| 4,479,494 A | 10/1984 | McEwen | |
| 4,605,010 A | 8/1986 | McEwen | |
| 4,770,175 A | 9/1988 | McEwen | |
| 5,048,536 A | 9/1991 | McEwen | |
| 5,181,522 A | 1/1993 | McEwen | |
| 5,312,431 A | 5/1994 | McEwen | |
| 5,352,195 A | 10/1994 | McEwen | |
| 5,366,474 A | * 11/1994 | Blumenkanz et al. | 606/202 |
| 5,439,477 A | 8/1995 | McEwen | |
| 5,454,831 A | 10/1995 | McEwen | |
| 5,556,415 A | * 9/1996 | McEwen et al. | 606/202 |
| 5,578,055 A | 11/1996 | McEwen | |
| 5,584,853 A | 12/1996 | McEwen | |
| 5,607,447 A | 3/1997 | McEwen et al. | |
| 5,649,954 A | 7/1997 | McEwen | |
| 5,681,339 A | 10/1997 | McEwen et al. | |
| 5,741,295 A | 4/1998 | McEwen | |
| 5,855,589 A | 1/1999 | McEwen et al. | |

\* cited by examiner

*Primary Examiner*—Kevin T. Truong
(74) *Attorney, Agent, or Firm*—Reed Smith LLP (57) ABSTRACT

A system and method of controlling the pressure within a pressure cuff of a surgical tourniquet so as selectively to occlude blood flow within a portion of a limb of a patient, wherein a sensor determines when flow past the tourniquet is occurring so that corrective action may be taken, such as by increasing the pressure in the tourniquet or by notifying an operator of the flow past the tourniquet. The present invention may use an acoustic sensor to detect Korotkoff sounds indicating incipient blood flow past the tourniquet. When such signals are detected, the tourniquet controller may either incrementally increase the pressure in the tourniquet, or if a threshold would be exceeded by such an increase, signal an alarm indicative of the blood flow.

35 Claims, 7 Drawing Sheets

SYSTEM AND METHOD FOR CONTROLLING PRESSURE IN A SURGICAL TOURNIQUET

The present application is a continuation in part of U.S. patent application Ser. No. 09/504,131, filed Feb. 25, 2000 now U.S. Pat. No. 6,475,228 which is a continuation of U.S. patent application Ser. No. 09/280,312 filed Mar. 29, 1999. U.S. patent application Ser. No. 09/280,312 issued as U.S. Pat. No. 6,051,016 on Apr. 18, 2000.

FIELD OF THE INVENTION

The present invention relates generally to surgical tourniquets. More particularly, the present invention relates to various aspects of a system and method for controlling pressure in a surgical tourniquet utilizing feedback from a flow detection sensor incorporated in the tourniquet control system.

BACKGROUND

Surgical tourniquets are widely used during surgical procedures to occlude the flow of blood in a portion of a limb during the procedure, particularly in connection with arthroscopic procedures relating to the hand, wrist, elbow, foot, and knee, in which the existence of a bloodless field in the appropriate portion of a patient's limb may be required. Surgical tourniquets are similarly useful in other procedures in which the creation of a bloodless field is desirable, including nerve grafting and harvesting. It is important that pressure be maintained by a surgical tourniquet despite the manipulation by a surgeon of the limb in which blood flow is being occluded, where the manipulation tends to affect the pressure within the tourniquet and the pressure distribution of the tourniquet on the extremity. Also, it is important that the tourniquet pressure be minimized to reduce the potential of adverse effects due to the constriction of the tourniquet. It is also important that the surgical tourniquet be easy to use and physically stable so that the surgeon may focus his attention on other aspects of the surgery.

Typical non-invasive blood pressure measurements are generally made by either of two methods. In the first method, a stethoscope is placed beneath or below a pressure cuff. The pressure cuff is then inflated to a pressure in excess of the patient's systolic blood pressure, causing occlusion of the blood flow past the pressure cuff. The pressure in the cuff is then gradually decreased, while a person taking the pressure measurement listens through the stethoscope. As the blood pressure overcomes the pressure in the cuff, blood begins flowing past the cuff. This blood flow causes sounds called Korotkoff sounds to be generated. These sounds are distinctive of the blood flow past the pressure cuff, and abate once the blood pressure fully reopens the arteries constricted by the pressure cuff. By identifying the Korotkoff sounds, and monitoring the decreasing pressure in the cuff, the pressure at which blood pressure exceeds cuff pressure can be identified. Determinations can be made of both systolic and diastolic blood pressures by monitoring Korotkoff sounds associated with a higher pressure (systolic) and a lower pressure (diastolic). This method is sometimes referred to as the auscultatory method.

A second method of non-invasive blood pressure measurement, called oscillometric measurement, is also accomplished using a pressure cuff and decreasing pressure. In oscillometric pressure measurement, however, a column of mercury is generally used to measure the pressure in the cuff. As the patient's blood pressure exceeds the cuff pressure, blood flow past the cuff causes the pressure in the cuff to pulse in time with the blood flow past the cuff. The mercury column being used to measure pressure thus also pulses, allowing a person taking the blood pressure measurement to visually identify blood flow past the pressure cuff. The patient's blood pressure can thus be determined by monitoring the mercury column for the start of pulsing, and the pressure at which the pulsing begins.

The pressure necessary to occlude blood flow in a tourniquet is dependant on the blood pressure of the patient on whom the tourniquet is applied. When the pressure of the tourniquet exceeds the blood pressure, the heart of the patient is unable to pump blood past the tourniquet location. Typically, the tourniquet pressure cuff is inflated in excess of the blood pressure to ensure occlusion of blood flow past the tourniquet. When a surgical tourniquet is applied to the arm, over-pressurization of the surgical tourniquet of 50–75 mm Hg is common. When a surgical tourniquet is applied to a leg, over-pressurization of the surgical tourniquet of 75–100 mm Hg is common.

Over-pressurization of a tourniquet can cause injury to a patient on whom the tourniquet is being used. Neural and vascular injuries can occur due to the pressure in use causing physical trauma. Accordingly, the pressure used to occlude blood flow past the tourniquet should be kept to the minimum necessary to overcome the systolic pressure, thus preventing the pumping of blood past the tourniquet. Contrarily, high pressures ensure occlusion of blood flow.

In addition to the constraints of simply using a surgical tourniquet to occlude blood flow, the use of the surgical tourniquet to provide a barrier to allow intravenous regional anesthesia (IVRA) raises additional concerns, particularly with the dangers associated with the flow of the anesthesia past the barrier and into the body of the patient. Furthermore, the need to flush the anesthesia from the limb at the conclusion of an operation requires the allowance of systolic flow to both test veins and arteries potentially affected by the surgery, and to displace the anesthesia used. The allowance of systolic flow while preventing diastolic flow requires accurate determination of the onset of flow past a surgical tourniquet or tourniquets being used to form the barrier.

SUMMARY OF THE INVENTION

The present invention is directed towards a system and method for controlling the pressure within a surgical tourniquet so as to occlude blood flow past a tourniquet. The surgical tourniquet uses a fluid medium to vary the pressure within the tourniquet. The fluid medium may be air. The addition or removal of air from the surgical tourniquet is controlled such as through a controller described in our patent applications, Ser. Nos. 09/280,312 and 09/504,131, herein incorporated in their entirety by reference thereto.

The flow of blood past a tourniquet creates a signal which is transmitted to the tourniquet by the physical contact between the patient and the tourniquet. The signal comprises pressure variations in the veins and arteries of an extremity to which the surgical tourniquet is applied. These pressure variations may be a signal audible to a listener, or a variation of the cuff pressure caused by the pulsing associated with normal blood flow. These pressure variations may be transmitted from the surgical tourniquet to the controller via the fluid medium used to inflate the tourniquet. By incorporating a sensor to detect these signals, a feedback loop can be incorporated into the controller allowing the controller to detect blood flow past the tourniquet when the tourniquet is inflated. When blood flow past the pressure cuff of the surgical tourniquet is detected, the controller can increase pressure into the surgical tourniquet, thereby providing a means for ensuring that the flow of blood past the surgical tourniquet is occluded.

In a first embodiment, the present invention is a surgical tourniquet controller which includes an occlusion sensor, and a means for increasing pressure in a surgical tourniquet when the occlusion sensor detects blood flow past the surgical tourniquet. The occlusion sensor may detect oscillometric indications or Korotkoff sounds as a means for detecting flow past the surgical tourniquet.

In an alternate embodiment, the present invention comprises a method for controlling a surgical tourniquet. The method includes the steps of inflating a pressure cuff to an initial pressure, detecting blood flow past a pressure cuff when blood flows past the pressure cuff, incrementally increasing pressure in the pressure cuff in response to detected flow past the pressure cuff, determining whether the increased pressure in the surgical tourniquet has occluded blood flow past the tourniquet, and when blood flow has not been occluded, continuing to incrementally increase blood cuff pressure until blood flow past the tourniquet is occluded, or may additionally incrementally increase the cuff pressure until a threshold pressure is achieved.

In a still further embodiment, the present invention comprises a computer readable medium for providing instructions to a surgical tourniquet controller, the medium tangibly embodying instructions which, when executed by a computer, cause a surgical tourniquet controller to inflate a pressure cuff to an initial pressure, detect blood flow past a pressure cuff when blood flows past the pressure cuff, incrementally increase pressure in the pressure cuff when flow is detected past the pressure cuff, determine whether the increased pressure in the pressure cuff has occluded blood flow past the pressure cuff, and when blood flow has not been occluded, continuing to incrementally increase blood pressure until blood flow past the pressure cuff is occluded.

Other features and advantages of the invention will be apparent from the following description of the preferred embodiment, and from the claims.

DETAILED DESCRIPTION OF THE INVENTION

Figure 1:
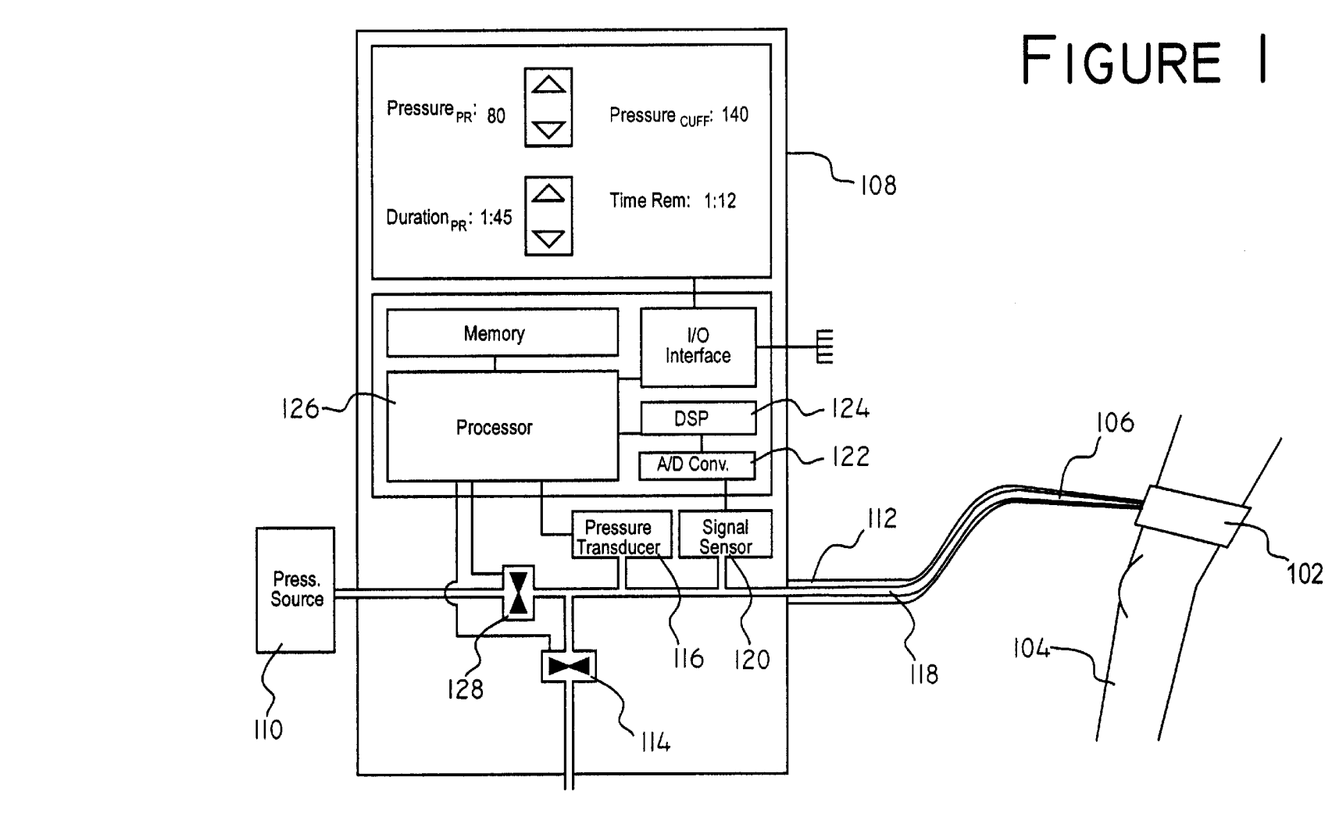
FIG. 1 is a block diagram illustrating the components of a basic surgical tourniquet controller according to the present invention.

Referring now to FIG. 1, wherein like reference numerals indicate like elements, there is shown the components of an embodiment of the present invention. A surgical tourniquet is a pressure cuff 102 containing a pressure chamber (not shown) which extends around the circumference of an appendage 104 in which it is desired to occlude blood flow. By increasing the pressure in the pressure chamber, the pressure cuff 102 compresses the appendix 104 until the constriction pressure exceeds the blood pressure, at which point internal veins and arteries close due to the inability of the blood pressure to overcome the pressure applied by the pressure cuff 102.

The pressure in the pressure chamber is controlled by adding or releasing a pressure medium 106 to or from the pressure chamber. The pressure medium 106 is a fluid allowing flow from the controller 108 into the pressure chamber. Pressure changes made to the pressure medium 106 at a location remote from the pressure cuff 102 are rapidly communicated to the pressure chamber when the pressure medium is a gas. Gaseous pressure mediums 106 are presently preferred, due to the ready availability of gases in the operating room environment. Although it is preferable to use air for the pressure medium 106 due to its free availability, other gasses or fluids may be used as conditions dictate. Furthermore, the use of a liquid, such as sterile distilled water, provides a better medium for the transmission of pressure signals from incipient blood flow.

Figure 3:
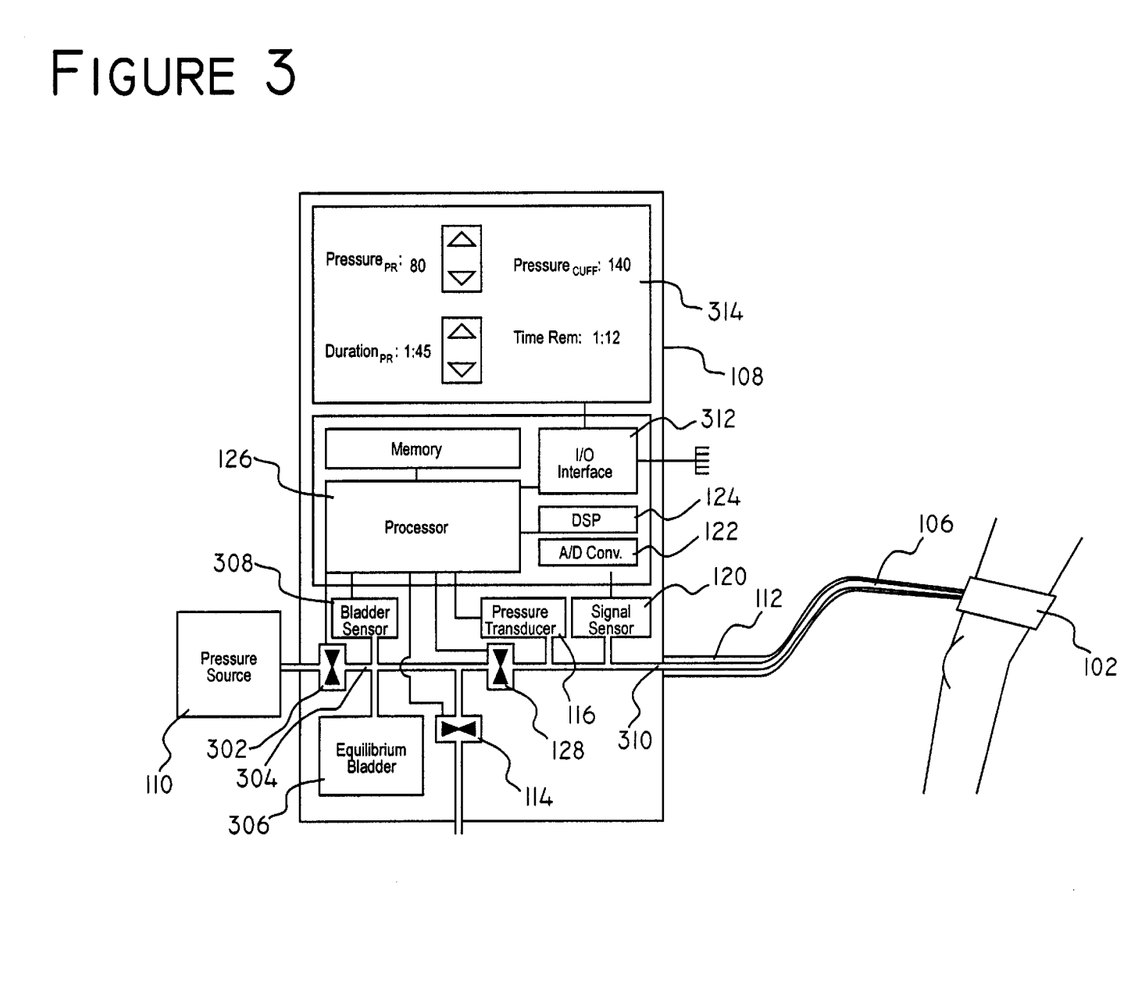
FIG. 3 is a block diagram illustrating the components of a surgical tourniquet controller according to the present invention, wherein the surgical controller includes additional controls and feedback loops for optimizing controller functionality.

In a typical controller 108, a source 110 of a pressurized flow medicum is connected to the supply tube 112 to increase pressure in the pressure chamber, while a release valve 114 is provided to bleed pressure from the pressure chamber to decrease pressure. These components may be located in the controller 108 to minimize the components that have to be collocated with the patient (not shown) during a medical procedure. As described in applicant's prior disclosures, an improved controller 108 may be provided by incorporating an inflatable bladder into the controller 108 (as shown in FIG. 3), thus allowing rapid changes to the pressure condition of the pressure cuff 102.

The pressure in a typical pressure cuff 102 is pre-set based upon medical considerations, which include the blood pressure of the patient, as well as safety factors to ensure that blood flow is occluded when the pressure cuff 102 is pressurized. The tourniquet pressure may be set at 75–100 mmHg above systolic blood pressure for a leg, or 50 to 75 mmHg above systolic blood pressure for an arm. A pressure sensor 116 is provided to measure the pressure in the pressure chamber of the pressure cuff 102. As the supply tube 112 provides flow communication between the pressure chamber and the controller 108, this pressure sensor 116 may be located in the controller 108 to further reduce the equipment which must be collocated with the patient.

The communicable path 118 that the pressure medium 106 forms may provide a path for flow signals to be transmitted from the pressure chamber to the controller 108. By placing a signal sensor 120 in communication with the pressure medium 106 either in the cuff or located in the controller, Korotkoff sounds and pressure variations indicating the onset of the flow of blood past a surgical cuff can be detected. From these indications, the controller can increase the cuff pressure if medically acceptable, and notify an operator of the incipient loss of blood occlusion. Rather than relying on blood pressure cuffs located on other portions of a patient's anatomy, the flow monitoring function is integrated within the tourniquet cuff, reducing the potential for disparities in measured conditions between a remote monitoring site and the tourniquet site. Furthermore, the direct monitoring of blood flow through the tourniquet allows the controller to use direct feedback, rather than a pressure off-set as a means of setting a pressure believed to be sufficient to occlude flow.

The selection of a fluid pressure medium is dependent on the capabilities of the sensor to be used to detect Korotkoff sounds or oscillometric variations in the cuff pressure. An incompressible liquid medium such as sterile distilled water provides an excellent medium for communicating pressure waves from a cuff through a supply tube to a remote controller. Concerns regarding the accidental discharge of the fluid medium into the surgical area should a cuff be accidentally punctured may necessitate for the use of a gaseous medium such as air to alleviate the potential problems associated with an accidental puncture. The use of air as a pressure medium, with its compressible nature however, requires greater sensitivity on the part of the sensor, as well as more rigorous digital signal processing to ensure detection of flow signals.

The sensor can be placed either in the cuff or in a controller. Where the sensor is placed in the cuff, pressure signal damping associated with the compressible nature of a gaseous pressure medium may require additional sensitivity on the part of the signal sensor as signals may be damped between the patient's extremity and the controller 108. In such a situation, the use of an incompressible fluid as a pressure medium may alleviate a portion of the damping associated with the use of a compressible medium such as a gas.

The signal sensor 120 may be a piezoelectric sensor which generates an electrical signal proportionate to the signal being transmitted via the pressure medium 106 from the pressure chamber to the signal sensor 120. The sensitivity of the signal sensor 120 must be selected based upon the frequency and magnitude of the flow signal being used for signal detection. Such signal sensors 120 are known and used for ambulatory blood pressure monitoring systems. The output of the signal sensor 120 typically is an analog electrical signal corresponding to the pressure variations detected by the signal sensor 120.

A signal sensor 120 which measures Korotkoff sounds must measure the pressure variations with sufficient sensitivity to measure the frequencies characterizing the Korotkoff sounds. The sounds may have a frequency in the kilohertz range. Accordingly, the sensor must have sufficient sampling frequency sensitivity to provide pressure measurements several times during each cycle associated with the sound being sensed. The pressure variations associated with the Korotkoff sounds are of small magnitude, thus requiring the signal sensor 120 to be able to detect small variations around a base pressure. By using a signal sensor 120 selected to detect acoustic signals, pressure variations within the pressure chamber can be ignored or filtered out.

A signal sensor 120 which measures pressure variations associated with a patient's pulse may not requires as high a frequency detection capability as a sensor used to detect Korotkoff. Blood pulses during a surgical procedure are on the order of 100 pulses or less per minute, although the pulses may occur more frequently in smaller patients. Again, the signal sensor 120 must measure the pressure multiple times during each pressure pulse to be able to adequately measure the pulsing for surgical tourniquet control purposes. The pressure range associated with the pressure pulses is determined by the difference between cuff pressure and peak blood pressure, such that a signal sensor 120 having lower technical capabilities, and therefore lower cost, may be implemented.

The signal sensor 120 is preferably connected to an analog to digital converter 122 (A/D converter) that converts the analog output of the sensor to a digital signal having timing and magnitude components. The sampling rate of the A/D converter 122 must be sufficient to obtain several samples per sensor signal cycle. The digitized sensor signal may then be communicated to a digital signal processor 124 (DSP), which determines from the digitized data whether blood is flowing past the pressure cuff 102 of the surgical tourniquet.

The DSP 124 may preferably generate a positive flow signal when flow is detected. The positive flow signal may preferably be an indication of each time blood flow is detected. Since the blood pressure in a patient is cyclic, Korotkoff sounds or a pressure signal indicative of a pulse will occur each time the patient's heart pumps blood past the pressure cuff 102. Each detection results in the generation of a positive flow signal. Positive flow signals are communicated to the processor 126. When the processor 126 receives a positive flow signal indicating blood flow past the pressure cuff 102, the processor 126 causes the pressure in the pressure cuff 102 to be incrementally increased. Thus, each time a positive flow signal is received by the processor 126, the pressure in the pressure cuff 102 is increased by opening the pressure source valve 128 to incrementally increase the pressure in the pressure cuff 102 until positive flow signals are no longer detected. The processor may then cause this pressure to be maintained, ensuring positive flow occlusion without relying on pressures significantly in excess of systolic blood pressure.

Basic Method of Controlling Pressure

Figure 2:
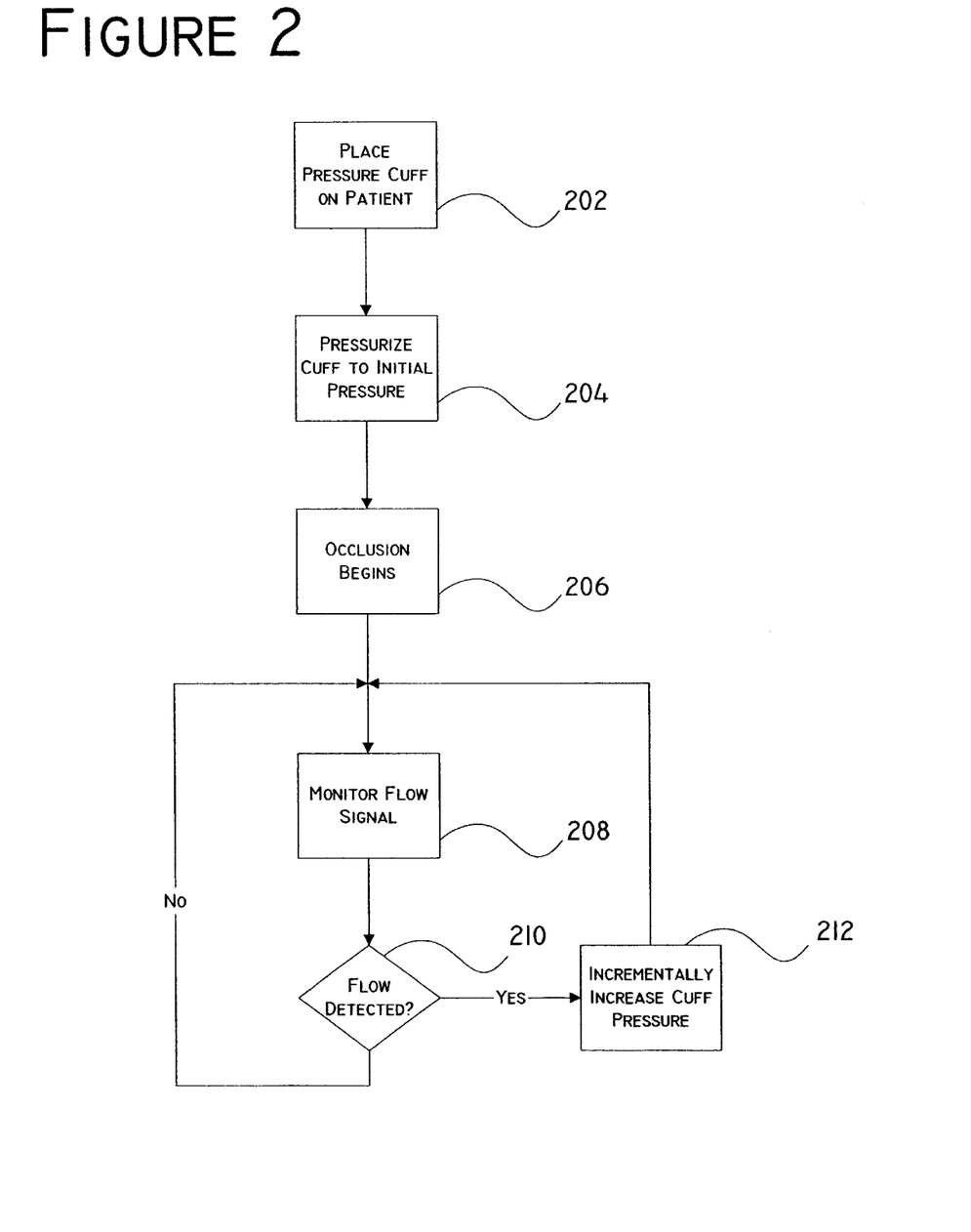
FIG. 2 is a process flowchart illustrating a method for controlling the occlusion of blood flow past a tourniquet according to the present invention.

The basic method of controlling a surgical tourniquet according to the present invention as shown in FIG. 2 thus relies on the generation of positive flow detection signals. The surgical tourniquet pressure cuff may be first placed 202 on the extremity of a patient whose blood flow is desired to be occluded. The pressure cuff may be initially pressurized 204 to an initial pressure, or may be left in an un-pressurized state. An occlusion start signal may be used to initiate the pressurization 206 of the pressure cuff until blood flow is occluded. Once the occlusion process is initiated, the sensor monitors 208 blood flow in the extremity past the cuff, generating a positive flow signal each time flow is detected 210. The pressure in the cuff is incrementally increased 212 until no more positive flow signals are received by the pressure controller. This method has the further advantage of correcting for pressure changes that may occur due to manipulations of the extremity on which the pressure has been applied.

Preferred Method of Controlling Pressure

Although the above basic method of controlling pressure embodies the present invention, the presently preferred embodiment of the invention incorporates additional functions associated with the control of a surgical tourniquet pressure cuff 102. As disclosed in our earlier applications, the controller 108 may use programming which assists a person such as a physician or anesthesiologist (hereafter collectively referred to as the operator) in setting and utilizing a pressure cuff 102 connected to the controller 108. Basic functions performed by the controller 108 may be to inform the person utilizing the controller of time constraints associated with the use of the surgical tourniquet, or with the pressures utilized with the surgical tourniquet.

In the presently preferred embodiment of the present invention, as shown in FIG. 3, a pressure source 110 is provided. The pressure source 110 maybe a pump which compresses ambient air to form the pressure medium 106. Alternate embodiments may utilize an external pressure medium source, such as a compressed gas source, such as a pressure tank (not shown). Alternately, should the pressure medium in use be a fluid, an external pressure source could be employed. A one-way valve 302 is preferably provided to prevent pressure in the system from bleeding of through the pressure source 110. The one way valve 302 is able to be opened upon command from the processor 126. When the one way valve 302 is opened, flow is restricted such that flow only occurs from the pressure source 110 to the pressure cuff path 304.

An equilibrium bladder 306 may be provided to increase the rate at which pressure can be increased in a pressure cuff 102. By having an equilibrium bladder 306, rapid inflation of the pressure cuff 102 can be accomplished without requiring a high flow pressure source. An equilibrium bladder pressure sensor 308 may be provided to allow the processor 126 to monitor the pressure in the equilibrium bladder 306.

The pressure cuff 102 of the surgical tourniquet is connected to the controller 108 via a supply tube 112 which conducts the pressure medium 106. The tube is connected to a port 310 on the side of the controller 108, connecting the pressure cuff 102 to the pressure source 110. A source valve 128 is located adjacent to the port 310, and allows the pressure cuff 102 and supply tube 112 to be isolated from the pressure source, equilibrium bladder, and exhaust valves.

The flow signal sensor 120 and a cuff pressure transducer 116 are connected to the pressure cuff path 304 between the port 310 and the source valve 128, such that the flow signal sensor 120 and cuff pressure transducer 116 are not isolated from the pressure cuff 102. The cuff pressure transducer 116 may be used to determine variations in the cuff pressure, such as due to a leak, or from changes resultant from the repositioning of a patient during a procedure.

The output of the signal sensor 120 is provided to an A/D converter 122, which passes the digitized signal to the digital signal processor 124, where the digitized output is analyzed for the presence of a flow signal. If a flow signal is detected, the central processor is so informed.

The controller 108 is also preferably provided with an input/output interface 312, which coordinates the flow of information to and from the controller 108. A first function of the I/O interface may be to allow an operator to provide input to the controller 108 through an operator interface 314, which may be a touch screen display on which menu-structured queries can be presented.

Figure 4A:
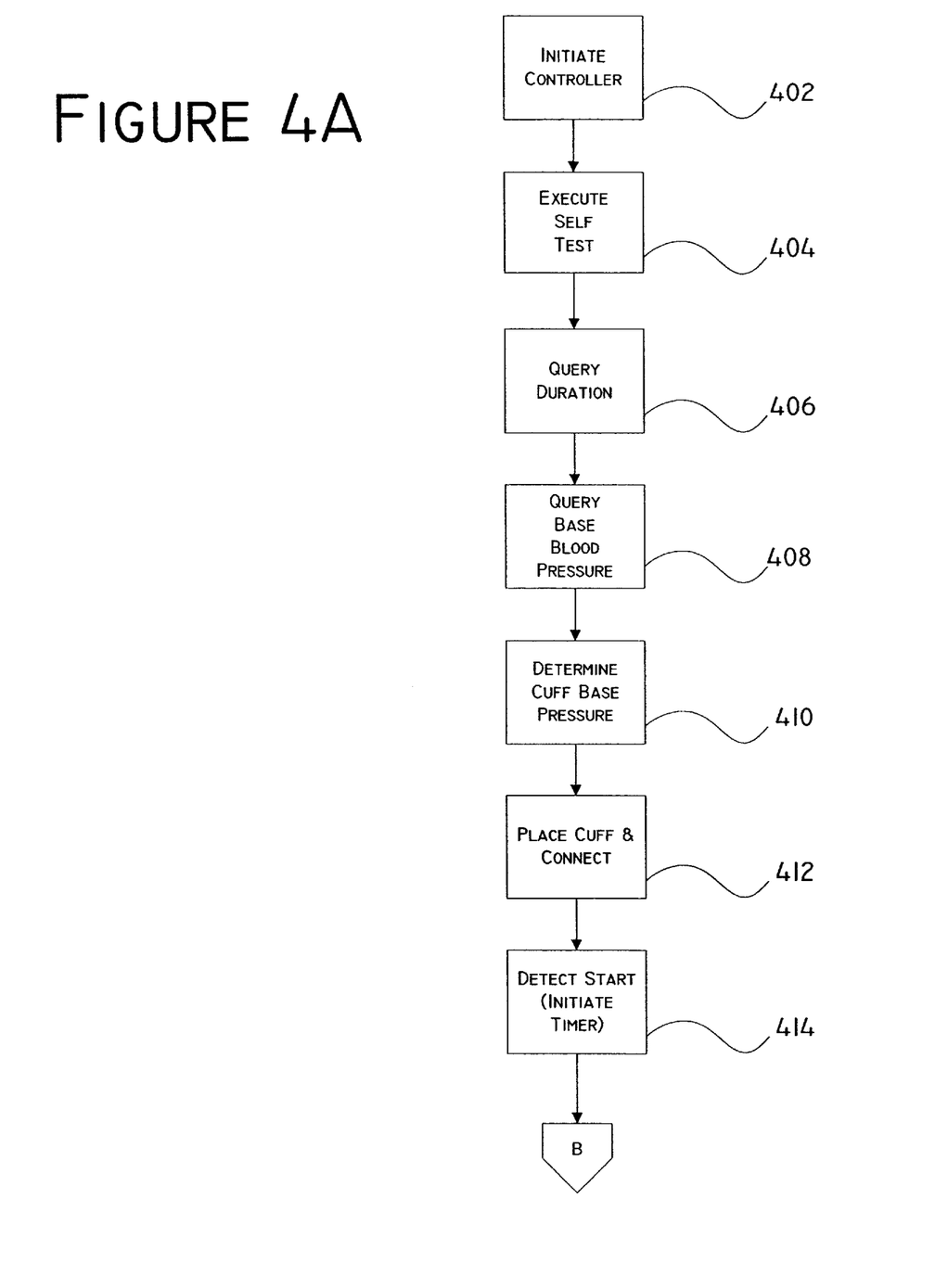
FIG. 4 is a process flowchart illustrating a method for controlling the occlusion of blood flow past a tourniquet utilizing blood pressure feedback such as in the system shown in FIG. 3.
Figure 4B:
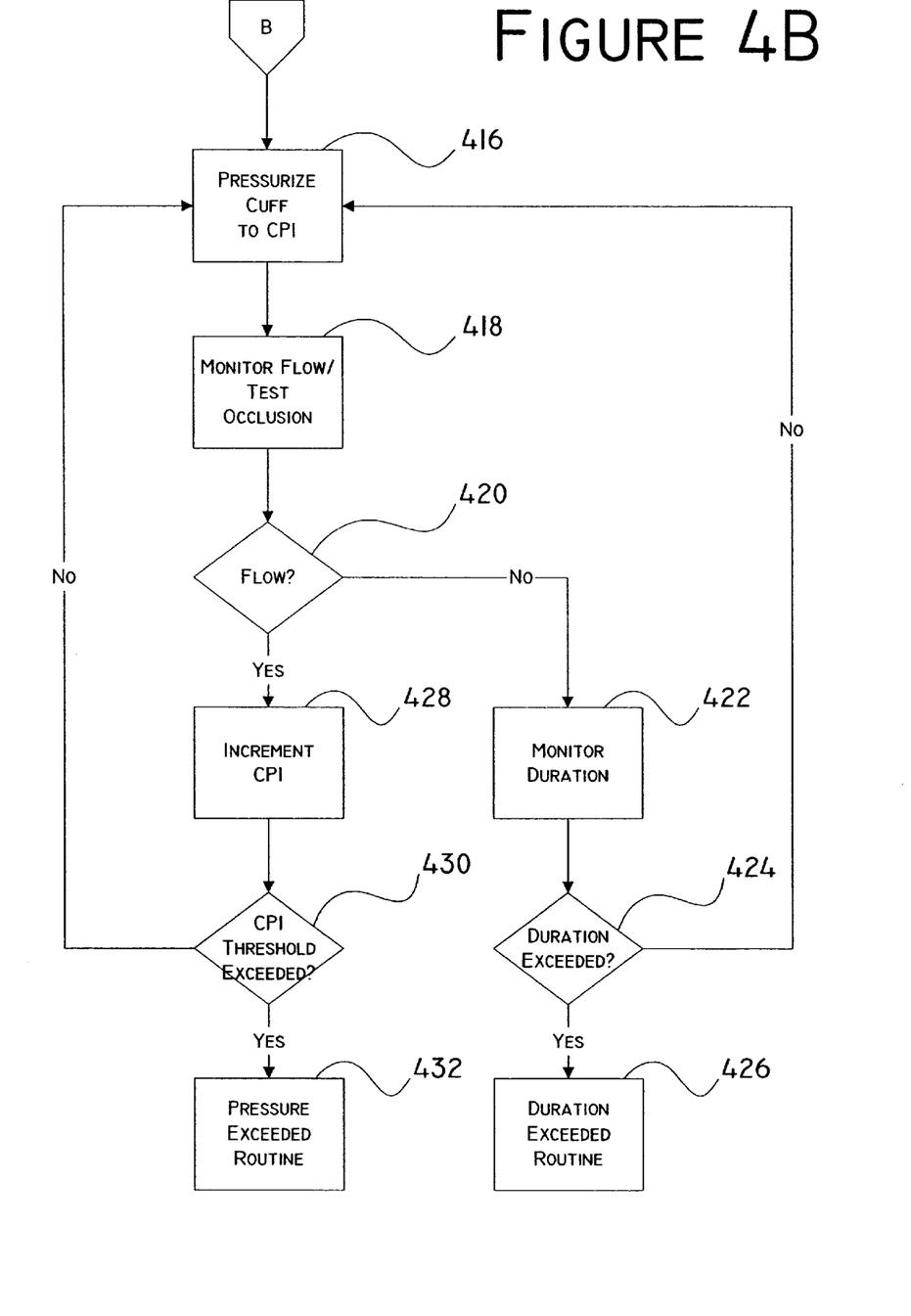

Accordingly, as shown in FIG. 4, the first step in the method of utilizing the presently preferred controller comprises first initiating 402 the controller. The initialization routine may preferably include the execution 404 of an internal self test verifying the circuitry of the controller, and the execution of the basic controller programming. Once the controller has performed these initiation functions, the controller may query 406 an operator to determine a desired inflation duration. This query can be conducted by displaying a duration setting field for an operator. Once the duration has been determined, the controller may also query 408 the operator for a base blood pressure. Where austatic signal detection is utilized, the pressure cuff must be initially pressurized to a level sufficient to at least partially occlude blood flow past a pressure cuff. Where oscillometric detection is implemented, sufficient initial pressure must be present in the pressure cuff to provide an adequate signal path between the pressure cuff and the sensor. Initial pressures may be suggested to the operator based on the extremity on which the tourniquet is to be placed, and/or the operator may be queried as to the blood pressure of the patient from which an initial pressure can be derived.

Once an initial pressure has been identified by an operator or set based on pre-programmed instructions, the controller may determine 410 a cuff base pressure based on the input provided by the operator. Where the operator has provided patient blood pressure, the controller may set an initial base pressure as an increment above patient blood pressure. Where the operator has specified a desired cuff pressure, the initial base pressure may be set equal to the desired cuff pressure. The cuff pressure inflation (CPI) may then be set to the base pressure.

Next, the pressure cuff may be placed 412 around the extremity of a patient for which blood flow is desired to be occluded. The pressure chamber of the cuff may then be connected by a pressure tube to the controller.

Once an occlusion initiation signal is detected 414 by the controller, the controller pressurizes 416 the pressure cuff to the CPI, and the sensor monitors 418 blood flow past the pressure cuff. As long as no blood flow past the pressure cuff is detected, the pressure controller monitors 418 the pressure in the cuff, and maintains the pressure in the cuff, while monitoring 422 the amount of time for which the pressure has been applied. Once it is determined 424 that the pressure has been applied for the selected duration, the controller may execute 426 a duration exceeded routine, including informing the operator that the programmed duration has expired. Alternately, the operator may manually end the blood flow occlusion by signaling the pressure controller to depressurize the cuff. If the pre-set duration has expired, the controller may signal the operator before depressurizing the cuff, allowing the operator to set an additional incremental duration.

The controller may also monitor the cuff pressure to ensure that safe pressures are maintained during the period in which blood flow is occluded. A maximum pressure may be pre-set by an operator, or a maximum pressure may be preset in memory associated with the controller. If a cuff pressure threshold is exceeded, a pressure exceeded routine may be implemented.

Once the pressure cuff has been pressurized to the initial pressure, blood flow past the pressure cuff may be monitored 418. If it is determined 420 that blood is flowing past the pressure cuff, the pressure controller determines whether an incrementally increased 428 pressure would exceed the maximum pressure. If it is determined 430 that the incrementally increased pressure would not exceed the maximum pressure, the pressure controller directs pressurization 416 of the pressure cuff to the incrementally increased pressure. If it is determined 430 that the incrementally increased pressure would exceed the maximum pressure, a pressure exceed routine may be executed 432, including generating an alarm to inform an operator that blood flow is not being fully occluded, and that the maximum pressure threshold has been achieved. At this point, the operator may over-ride the maximum pressure and set a higher maximum pressure, or may cause a medical procedure to be ended due to the blood flow past the tourniquet. If the maximum pressure is re-set to a higher level, the pressure controller may continue to incrementally increase the cuff pressure in response to positive flow signals until blood flow is occluded, or until the new maximum pressure is achieved.

Alternate Embodiments

Figure 5:
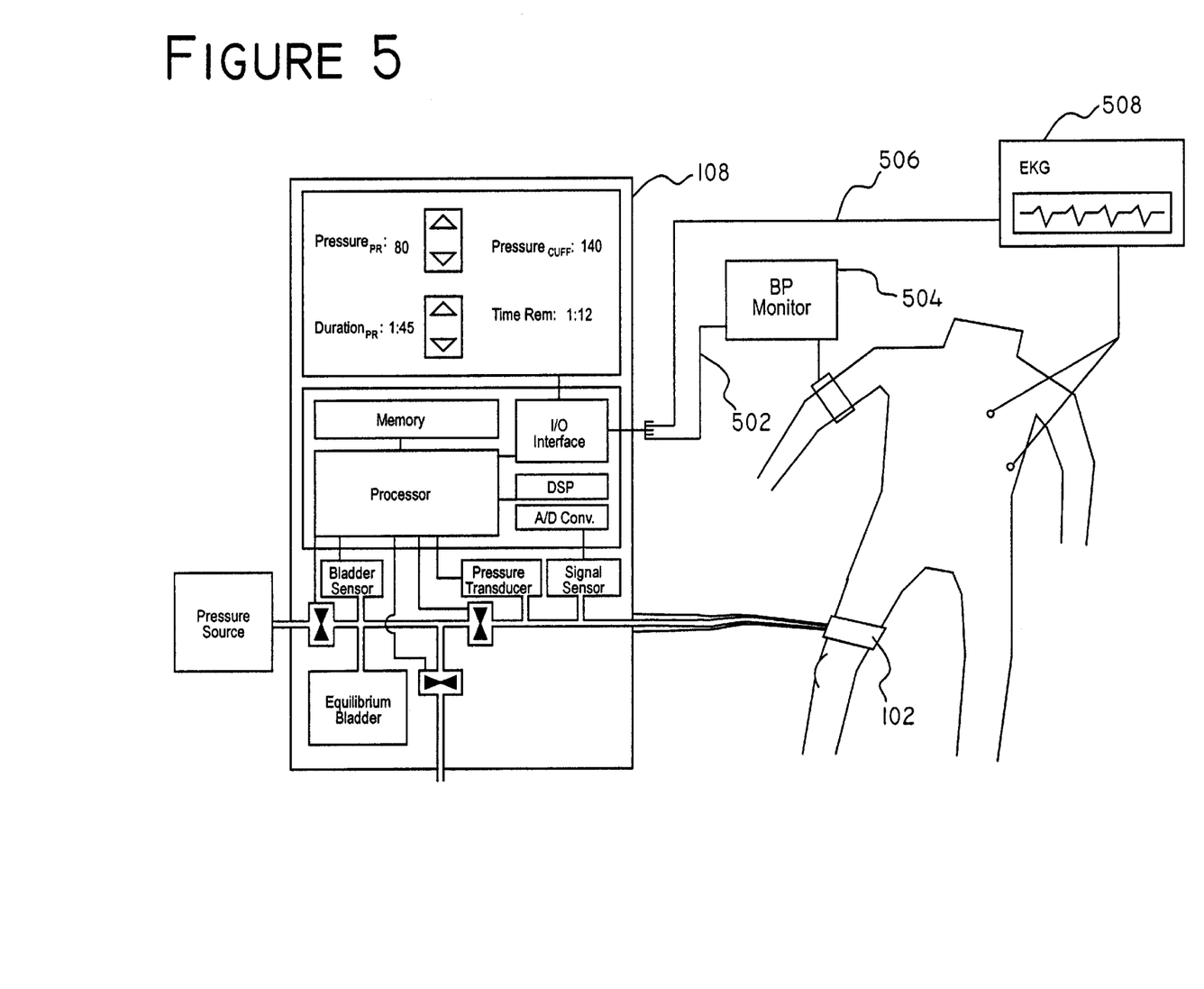
FIG. 5 is a block diagram illustrating the use of the present invention in an operating room environment in accordance with the present invention.

In addition to the feedback provided by the flow detection sensor, the surgical tourniquet controller may be provided with additional feedback sources. As shown in FIG. 5, a feedback signal 502 informing the controller of systolic pressure from a blood pressure monitor 504 may be implemented such that the controller may set cuff pressure dependant upon the systolic pressure, while providing flow detection measurement to ensure that blood flow is occluded. The systolic pressure feedback system may utilize pressures determined by invasive or non-invasive methods.

An alternate feedback loop may be provided by providing a heart rate or electrocardiogram signal (EKG) 506 from an EKG monitor 508 to the controller 108, allowing flow signals to be correlated to heart beats. Providing a heart rate or EKG signal 506 would allow non-flow related noises to be filtered out based on the beating of the heart.

Alternately, detected signals and associated data could be transmitted from the STC to other medical equipment by implementation of an output port (not shown). Such a port could be utilized to allow data associated with a medical procedure to be recorded and stored for addition to a patient medical record, or to a controller utilization record.

Figure 6:
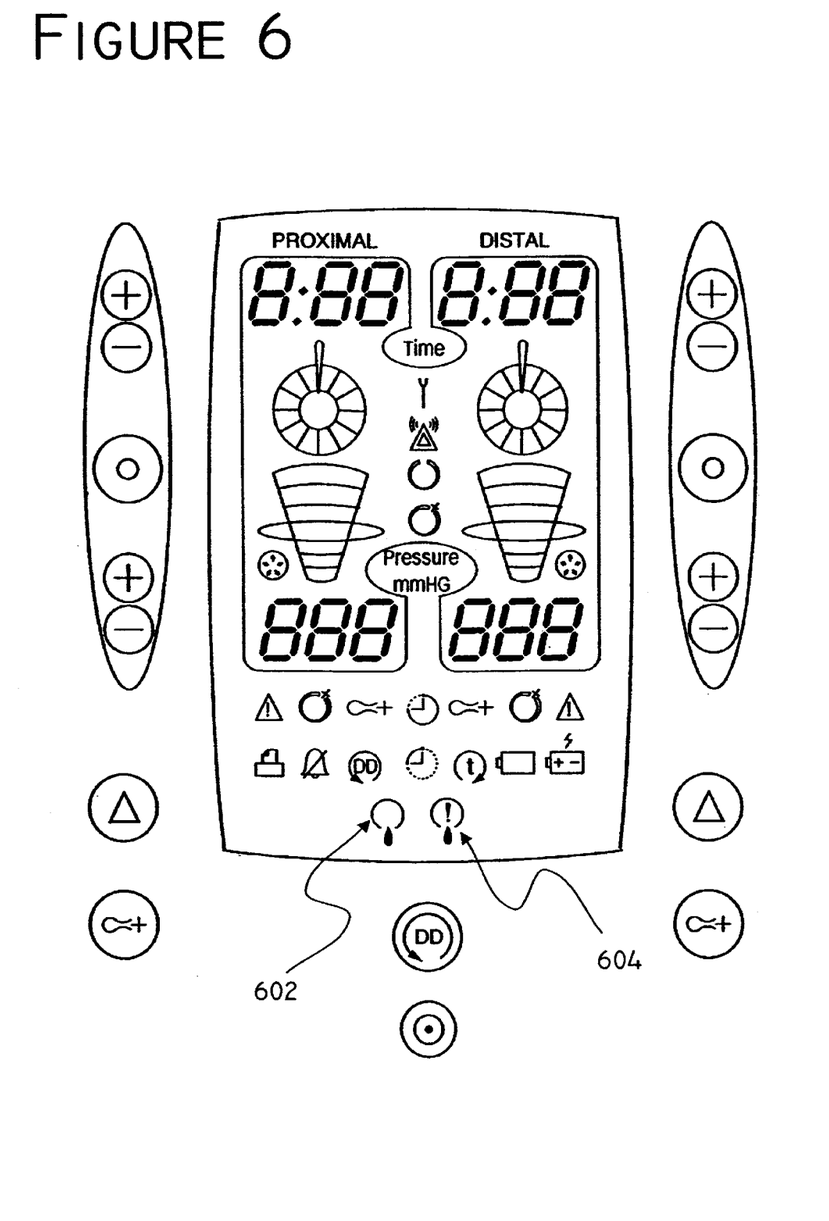
FIG. 6 is an illustration of an operator input/output interface for use with the present invention.

As shown in FIG. 6, the display of the STC may include multiple functions. The display may include an iconic indicator 602 of detected blood flow past the pressure cuff, or a iconic indication 604 indicating that a maximum pressure has been reached and blood flow past the pressure cuff is still being detected.

The flow detection indicators may be programmed to illuminate for a timed period after a flow detection occurs, such that after a specific period of time or number of heartbeats, the indicator is extinguished unless additional flow past the pressure cuff is detected.

The present invention may be embodied in other specific forms without departing from the spirit or essential attributes of the invention. Accordingly, reference should be made to the appended claims, rather than the foregoing specification, as indicating the scope of the invention.

What is claimed is:

1. A surgical tourniquet controller, said controller comprising:
    a pressure source, said pressure source supplying a pressure medium at a sufficient pressure to pressurize a pressure cuff being used as a surgical tourniquet;
    a pressure port, said pressure port allowing a pressure medium to be supplied to a pressure cuff;
    a source valve, said source valve interposed between said pressure source and said pressure port;
    an occlusion sensor, said occlusion sensor detecting pressure variations in the pressure medium indicative of blood flow past a pressure cuff, said occlusion sensor further generating a flow signal indicative of blood flow past a pressure cuff; and
    a processor, said processor communicably connected to said occlusion sensor, said processor further communicably connected to said source valve;
    wherein said processor instructs said source valve to increase the pressure in a pressure cuff when blood flow is detected past the pressure cuff.

2. A surgical tourniquet controller according to claim 1, further comprising a pressure threshold value, wherein said processor instructs said source valve to increase the pressure in a pressure cuff only when the increased pressure would not exceed the pressure threshold value.

3. A surgical tourniquet controller according to claim 1, further comprising a pressure relief valve, said pressure relief valve having a pre-determined pressure threshold value, said pressure relief valve being connected to said pressure port such that if a pressure in said pressure port exceeds said pressure threshold value, said pressure relief valve vents said pressure port.

4. A surgical tourniquet controller according to claim 1, wherein said occlusion sensor senses Korotkoff sounds.

5. A surgical tourniquet controller according to claim 4, wherein said surgical tourniquet controller further comprises an analog to digital converter and a digital signal processor, said analog to digital converter converting an analog output from said occlusion sensor into a digital signal, said digital signal processor analyzing said digital signal to identify flow past a pressure cuff.

6. A surgical tourniquet controller according to claim 5, further comprising an input/output interface.

7. A surgical tourniquet controller according to claim 6, further comprising a heart rate sensor, said heart rate sensor generating a heart rate signal indicative of a heart rate associated with a patient to whom a surgical tourniquet has been applied, said heart rate sensor further communicating said heart rate signal to said surgical tourniquet controller, said surgical tourniquet controller using said heart rate signal to provide feedback for flow detection.

8. A surgical tourniquet controller according to claim 7, wherein said heart rate sensor is an EKG monitor.

9. A surgical tourniquet controller according to claim 1, wherein said occlusion sensor senses oscillometric indications of blood flow past a pressure cuff.

10. A surgical tourniquet controller according to claim 1, further comprising an input/output interface.

11. A surgical tourniquet controller according to claim 10, further comprising a heart rate sensor, said heart rate sensor generating a heart rate signal indicative of a heart rate associated with a patient to whom a surgical tourniquet has been applied, said heart rate sensor further communicating said heart rate signal to said surgical tourniquet controller, said surgical tourniquet controller using said heart rate signal to provide feedback for flow detection.

12. A surgical tourniquet controller according to claim 11, wherein said heart rate sensor is an EKG monitor.

13. A surgical tourniquet controller according to claim 10, further comprising a blood pressure sensor, said blood pressure sensor generating a blood pressure signal indicative of a patient's blood pressure said blood pressure sensor further communicating said blood pressure signal to said surgical tourniquet controller, said surgical tourniquet controller using said blood pressure signal to set an initial cuff pressure value.

14. A surgical tourniquet controller according to claim 10, further comprising a blood pressure sensor, said blood pressure sensor generating a blood pressure signal indicative of a patient's blood pressure said blood pressure sensor further communicating said blood pressure signal to said surgical tourniquet controller, said surgical tourniquet controller using said blood pressure signal to verify that a cuff pressure value exceeds said blood pressure signal.

15. A surgical tourniquet controller according to claim 1, further comprising a graphical display, said graphical display graphically displaying an iconic indicator when blood flow past a pressure cuff is detected.

16. A surgical tourniquet controller according to claim 1, further comprising a graphical display and a maximum pressure threshold, said graphical display graphically displaying an iconic indicator when blood flow past a pressure cuff is detected and when said cuff pressure is equal to or exceeds said maximum pressure threshold.

17. A surgical tourniquet controller, said controller comprising:
    an occlusion sensor, said occlusion sensor detecting blood flow past a pressurized pressure cuff, said occlusion signal further generating a signal indicative of detected blood flow; and
    a means for increasing the pressure in a pressure cuff in response to a signal indicating detected blood flow.

18. The surgical tourniquet controller of claim 17, wherein said occlusion sensor comprises a sensor which measures flow sounds associated with blood flow past a pressure cuff.

19. The surgical tourniquet controller of claim 17, wherein said occlusion sensor comprises a sensor which measures pressure fluctuations in a pressure cuff associated with blood flow past a pressure cuff.

20. The surgical controller of claim 17, further comprising a heart sensing means, said heart sensing means sensing a heart beat signal associated with a patient to whom a pressure cuff has been applied, said heart beat signal being communicated to said means for sensing occlusion, wherein said means for sensing occlusion further uses said heart beat signal for identifying flow past a pressure cuff.

21. A method for controlling a surgical tourniquet, said method comprising the steps of:

inflating a pressure cuff to an initial pressure;

detecting blood flow past a pressure cuff;

incrementally increasing pressure in the pressure cuff in response to detected flow past the pressure cuff;

determining whether the increased pressure in the surgical tourniquet has occluded blood flow past the tourniquet;

when blood flow has not been occluded, continuing to incrementally increase pressure in the pressure cuff until blood flow past the tourniquet is occluded or a maximum pressure threshold is reached.

22. A method for controlling a surgical according to claim 21, further comprising the steps of:

receiving a desired inflation duration;

starting a timer when the pressure cuff is initially inflated; and deflating the pressure cuff when the desired inflation duration has occurred.

23. A method for controlling a surgical according to claim 21, further comprising the steps of:

receiving a desired inflation duration;

starting a timer when the pressure cuff is initially inflated;

informing an operator when the desired inflation duration has occurred; and deflating the pressure cuff upon command by an operator.

24. A method for controlling a surgical according to claim 21, further comprising the steps of:

determining a threshold pressure above which the pressure cuff should not be inflated;

ceasing incremental pressure increases when the threshold pressure is achieved; and informing an operator that the threshold pressure has been achieved.

25. A method for controlling a surgical according to claim 21, further comprising the steps of:

receiving a threshold pressure above which the pressure cuff should not be inflated from an operator;

ceasing incremental pressure increases if the threshold pressure is reached; and informing an operator that the threshold pressure has been reached.

26. A computer readable medium tangibly embodying instructions which, when executed by a computer, cause a surgical tourniquet controller to:

inflate a pressure cuff to an initial pressure;

receive indications from a sensor of blood flow past a pressure cuff when blood flows past the pressure cuff;

incrementally increase pressure in the pressure cuff when blood flow past a pressure cuff is detected;

determine whether the increased pressure in the pressure cuff has occluded blood flow past the pressure cuff; and when blood flow has not been occluded, continuing to incrementally increase blood pressure until blood flow past the pressure cuff is occluded.

27. A computer readable medium tangibly embodying instructions according to claim 26, wherein the instructions when executed further cause a surgical tourniquet controller to:

receive a desired inflation duration;

start a timer when a pressure cuff is initially inflated; and to deflate the pressure cuff when the desired inflation duration has occurred.

28. A computer readable medium tangibly embodying instructions according to claim 26, wherein the instructions when executed further cause a surgical tourniquet controller to:

receive a desired inflation duration;

start a timer when a pressure cuff is initially inflated;

signal an operator when the desired inflation duration has occurred;

receive a deflate command from an operator; and deflate the pressure cuff upon receipt of the command from an operator.

29. A computer readable medium tangibly embodying instructions according to claim 26, wherein the instructions when executed further cause a surgical tourniquet controller to:

determine a threshold pressure above which the pressure cuff should not be inflated;

cease incremental pressure increases when the threshold pressure is achieved; and inform an operator that the threshold pressure has been achieved.

30. A surgical tourniquet system, including a pressure cuff that may be closed around a patient's limb so as to exert pressure on blood vessels within a portion of the limb, comprising:

an inflatable cuff containing a first quantity of gas having a first internal pressure;

an inflatable bladder containing a second quantity of gas having a second internal pressure;

a first conduit between said inflatable cuff and said inflatable bladder;

a first valve within said first conduit;

a controller connected to said first valve; and a flow sensor connected to said first conduit, said flow sensor between said first valve and said inflatable cuff, wherein, when the pressure in said inflatable cuff is greater than that in said inflatable bladder, said controller decreases the pressure in said inflatable cuff by opening said first valve;

wherein, when the pressure in said inflatable cuff is less than that in said inflatable bladder, said controller increases the pressure in said inflatable cuff by opening said first valve; and wherein when the flow sensor detects flow past the inflatable cuff, the second internal pressure in the inflatable bladder is incrementally increased.

31. The surgical tourniquet system of claim 30, further comprising:
   a pump connected to said controller;
   a second conduit between said pump and said inflatable bladder;
   a second valve within said second conduit and connected to said controller,
   wherein said controller increases the pressure in said inflatable bladder by opening said second valve and pumping gas from outside the surgical tourniquet system into said inflatable bladder; and
   wherein said controller decreases the pressure in said inflatable bladder by opening said second valve, thereby equalizing the pressure in said inflatable bladder with that of the atmosphere.

32. A method of controlling the pressure within a surgical tourniquet system so as selectively to occlude blood flow within a portion of a limb of a patient, comprising the steps of:
   (a) decreasing the pressure within an inflatable cuff surrounding a portion of a limb of a patient by automatically opening a first valve connected to a controller and located within a first conduit between an inflatable bladder and the inflatable cuff, when the pressure in the inflatable cuff is greater than that in the inflatable bladder;
   (b) increasing the pressure within an inflatable cuff surrounding a portion of a limb of a patient by automatically opening a first valve connected to a controller and located within a first conduit between an inflatable bladder and the inflatable cuff, when the pressure in the inflatable cuff is less than that in the inflatable bladder; and
   (c) when flow past an inflatable cuff is detected, incrementally increasing the pressure within an inflatable bladder.

33. A surgical tourniquet system, comprising:
   an inflatable cuff;
   a controller connected to said inflatable cuff;
   a flow sensor; and
   a display connected to said controller,
   wherein a user controls the surgical tourniquet system by means of a graphical user interface displayed on said display.

34. The surgical tourniquet system of claim 33, wherein the graphical user interface comprises a plurality of icons, at least one of said icons being a flow detected indication icon.

35. The surgical tourniquet system of claim 33, wherein the graphical user interface comprises a plurality of icons, at least one of said icons being a threshold pressure achieved flow detected indication icon.

* * * * *